United States Patent
Peng et al.

(10) Patent No.: US 11,828,761 B2
(45) Date of Patent: Nov. 28, 2023

(54) METHOD FOR DETECTING AFLATOXIN B1 BASED ON FLUORESCENT COPPER NANOPARTICLES

(71) Applicant: Jiangnan University, Wuxi (CN)

(72) Inventors: Chifang Peng, Wuxi (CN); Min Li, Wuxi (CN); Shengmei Tai, Wuxi (CN); Xinlin Wei, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 17/826,480

(22) Filed: May 27, 2022

(65) Prior Publication Data

US 2022/0291208 A1 Sep. 15, 2022

Related U.S. Application Data

(63) Continuation of application No. PCT/CN2021/118667, filed on Sep. 16, 2021.

(30) Foreign Application Priority Data

Jun. 7, 2021 (CN) .......................... 202110632202.8

(51) Int. Cl.
*G01N 33/58* (2006.01)
*G01N 21/64* (2006.01)
(Continued)

(52) U.S. Cl.
CPC ............ *G01N 33/582* (2013.01); *B82Y 15/00* (2013.01); *B82Y 40/00* (2013.01);
(Continued)

(58) Field of Classification Search
CPC .......... B82Y 5/00; B82Y 15/00; B82Y 30/00; B82Y 40/00; G01N 21/6428; G01N 33/02;
(Continued)

(56) References Cited

U.S. PATENT DOCUMENTS

2007/0109536 A1  5/2007  Weiss et al.

FOREIGN PATENT DOCUMENTS

| CN | 103725686 A | 4/2014 |
| CN | 104422686 A | 3/2015 |

(Continued)

*Primary Examiner* — Jeremy C Flinders
(74) *Attorney, Agent, or Firm* — IPro, PLLC; Na Xu

(57) ABSTRACT

Disclosed is a method for detecting aflatoxin B1 based on fluorescent copper nanoparticles, belonging to the technical fields of analytical chemistry, materials science and nano biosensing. In the disclosure, β-CD@DNA-Cu NMs are prepared by using Y-shaped DNA as a template, ascorbic acid as a reducing agent and β-CD as a fluorescence stabilizing and enhancing agent. Then, a ratiometric fluorescent probe is constructed based on the β-CD@DNA-Cu NMs. Finally, the detection of AFB1 with high sensitivity, high selectivity and high accuracy is achieved by using the fluorescent probe. According to the method of the disclosure, in linear ranges of 0.03-10 ppb and 10-18 ppb, a ratio value of $I_{433}$ nm/$I_{650}$ nm and a concentration of AFB1 exhibit a good linear relationship respectively, and a limit of detection is 0.012 ppb (S/N=3). Metal ions $Ca^{2+}$ may be replaced with $Yb^{3+}$, $Y^{3+}$, $Er^{3+}$ and $Pt^{2+}$, which are also suitable for increasing sensitivity of AFB1 in rice.

16 Claims, 5 Drawing Sheets

Specification includes a Sequence Listing.

(51) Int. Cl.
*B82Y 15/00* (2011.01)
*B82Y 40/00* (2011.01)
*G01N 33/02* (2006.01)

(52) U.S. Cl.
CPC ......... *G01N 21/6428* (2013.01); *G01N 33/02* (2013.01); *G01N 2333/38* (2013.01)

(58) Field of Classification Search
CPC ............ G01N 33/582; G01N 2333/37; G01N 2333/38
See application file for complete search history.

(56) References Cited

FOREIGN PATENT DOCUMENTS

| | | | |
|---|---|---|---|
| CN | 104962615 A | | 10/2015 |
| CN | 105056213 A | * | 11/2015 |
| CN | 107764784 A | | 3/2018 |
| CN | 109342526 A | | 2/2019 |
| CN | 109406475 A | | 3/2019 |
| CN | 112444510 A | | 3/2021 |
| CN | 112662742 A | | 4/2021 |
| CN | 112816450 A | | 5/2021 |
| CN | 113281320 A | | 8/2021 |
| WO | 2020141498 A1 | | 7/2020 |

* cited by examiner

SEQUENCE LISTING

<160> NUMBER OF SEQ ID NOS: 3

<210> SEQ ID NO 1
<211> LENGTH: 26
<212> TYPE: DNA
<213> ORGANISM: Artificial Sequence
<220> FEATURE:
<223> OTHER INFORMATION: Synthetic DNA

<400> SEQUENCE: 1
cctgtctgcc taatgtgcgt cgtaag                                26

<210> SEQ ID NO 2
<211> LENGTH: 26
<212> TYPE: DNA
<213> ORGANISM: Artificial Sequence
<220> FEATURE:
<223> OTHER INFORMATION: Synthetic DNA

<400> SEQUENCE: 2
cttacgacgc acaaggagat catgag                                26

<210> SEQ ID NO 3
<211> LENGTH: 26
<212> TYPE: DNA
<213> ORGANISM: Artificial Sequence
<220> FEATURE:
<223> OTHER INFORMATION: Synthetic DNA

<400> SEQUENCE: 3
ctcatgatct cctttaggca gacagg                                26

METHOD FOR DETECTING AFLATOXIN B1 BASED ON FLUORESCENT COPPER NANOPARTICLES

TECHNICAL FIELD

The disclosure relates to a method for detecting aflatoxin B1 based on fluorescent copper nanoparticles, belonging to the technical fields of analytical chemistry, materials science and nano biosensing.

BACKGROUND

Aflatoxins (AFTs), one of the most common contaminants in grains, are a category of mycotoxins that are widespread in nature and have high teratogenicity, carcinogenicity and physiological and metabolic toxicity. Among them, aflatoxin B1 (AFB1) is the most toxic and carcinogenic, and has been classified as a Group I carcinogen by the International Agency for Research on Cancer (IARC). Long-time exposure to food containing low level of aflatoxins will lead to cumulative toxicity in the liver and cause liver damage, liver cancer and the like, thus seriously threatening human health and even life. Traditional methods for detecting aflatoxins are mainly based on instrumental analysis, for example, high-performance liquid chromatography (HPLC) and liquid chromatography-mass spectrometry (LC-MS). Despite their high sensitivity and accurate and reliable measured results, their application in on-site rapid screening is greatly limited because they require a lot of organic solvents, expensive equipment, high time cost and professional operators. At present, the rapid detection of AFB1 is mainly based on immunoassay, but the preparation period of antibodies is long and the cost is high.

In recent years, fluorescence detection has attracted much attention because of its advantages including high sensitivity, specificity, economy and simple operation. AFB1 is fluorescent, according to which the fluorescence detection can be developed. However, the fluorescence of AFB1 is easily quenched in a solvent, which reduces the detection sensitivity. ZHANG Min et al. (literature 1: ZHANG Min, GUO Ting, LIU Xin, XIAO Jie, ZHANG Yuhao, M A Liang. Research on Mechanisms Underlying Fluorescence Enhancement of Aflatoxin B1 by β-cyclodextrin and Its Derivatives [J]. Food Science, 2012, 33(15):28-33; literature 2: ZHANG Min, ZHANG Yuhao, M A Liang. Research on Fluorescence Spectrophotometry of Synergistic enhancement of Aflatoxin B1 by β-cyclodextrin and Its Derivatives and Metal Ions and Its Application [J]. Analytical Chemistry, 2011, 39(12):1907-1911) used β-cyclodextrin (β-CD) to enhance the fluorescence intensity of AFB1, thus increasing its detection sensitivity. On this basis, a β-cyclodextrin and its derivatives (β-CDs)-metal ion (M) system was further constructed to enhance the fluorescence of aflatoxin B1. The principle is: AFB1 can enter the cavity of β-CD to form inclusion compounds, which makes the solubility higher, prevents the solvent from quenching the fluorescence of these substances, and thus gains higher fluorescence and stability; and some metal ions, especially $Hg^{2+}$, can form a metal chelate compound with AFB1, which can greatly enhance the fluorescence intensity of AFB1. Although this method exhibits high sensitivity, it requires the addition of toxic heavy metal elements, and the single-signal mode used is susceptible to interference from concentration of the probe, drift of the light source or detector, and environmental factors in complex matrices.

The ratiometric detection mode, which uses one or more other signals independent of the sensing signal as an internal standard and outputs a ratio of two types of signals as the signal, can effectively overcome the above defects in the signal of the single-signal probe, thereby enhancing the accuracy of the detection results.

Metal fluorescent nanomaterials (gold, silver, copper) have the advantages of low toxicity, large Stokes shift and photobleaching resistance. Modifying the nanomaterials with β-CD, which can recognize guest molecules, can achieve enrichment of the guest molecules on the surface of the nanomaterials and sensitive detection of the guest molecules. As in literature 3 (LI Y, WEN Q-L, LIU A-Y, et al. One-pot synthesis of green-emitting gold nanoclusters as a fluorescent probe for determination of 4-nitrophenol [J]. Microchim Acta, 2020, 187(2):.), sensitive fluorescence detection of 4-nitrophenol can be achieved by using β-CD modified gold nanoclusters.

As food safety regulations become increasingly strict with the residue limit of AFB1 in food, there are still no relevant studies reporting the detection of AFB1 with high sensitivity, high selectivity and high accuracy by using a simple fluorescent nanoprobe.

SUMMARY

Technical Problems

At present, as food safety regulations become increasingly strict with the residue limit of AFB1 in food, it is still challenging to achieve detection of AFB1 with high sensitivity, high selectivity and high accuracy by using a simple fluorescent nanoprobe.

Technical Solution

In order to solve at least one of the problems above, in the disclosure, copper nanomaterials β-CD@DNA-Cu NMs are prepared by using Y-shaped DNA (Y-shaped complementary nucleic acid duplex) as a template, ascorbic acid (AA) as a reducing agent and mono-(6-mercapto-6-deoxy)-β-cyclodextrin (β-CD) as a fluorescence stabilizing and enhancing agent; then, a ratiometric fluorescent probe is constructed based on the β-CD@DNA-Cu NMs; and finally, the detection of AFB1 with high sensitivity, high selectivity and high accuracy is achieved by using the fluorescent probe.

A first object of the disclosure is to provide a method for preparing fluorescent copper nanoparticles β-CD@DNA-Cu NMs, including the following steps:

(1) Preparation of DNA-Cu NMs;

mixing a template strand Y-shaped DNA solution and an ascorbic acid solution uniformly, then adding a cupric acetate solution, and mixing the mixture uniformly to obtain a DNA-Cu NMs solution; and (2) β-CD Modified DNA-Cu NMs:

mixing the DNA-Cu NMs solution obtained in step (1) and a β-CD solution uniformly, and performing ultrafiltration to obtain the β-CD@DNA-Cu NMs.

In an embodiment of the disclosure, the template strand Y-shaped complementary nucleic acid duplex (Y-shaped DNA) in step (1) is prepared by a method according to the literature (Meng, H. M.; Zhang, X.; Lv, Y.; Zhao, Z.; Wang, N. N.; Fu, T.; Fan, H.; Liang, H.; Qiu, L.; Zhu, G.; Tan, W. DNA Dendrimer: An Efficient Nanocarrier of Functional Nucleic Acids for Intracellular Molecular Sensing. ACS Nano 2014, 8, 6171-6181.). The method specifically includes:

mixing three oligonucleotide strands ($Y_{0a}$, $Y_{0b}$, $Y_{0c}$) equally in an MOPS buffer to obtain a mixed solution; then heating the mixed solution to 90° C., and after 5 min of denaturation, slowly cooling the mixed solution to room temperature to obtain the Y-shaped DNA; and storing the Y-shaped DNA solution in a refrigerator at −18° C., where the MOPS buffer has a concentration of 5-20 mM, a concentration of NaAc is 75-300 mM, a concentration of $MgCl_2$ is 1-10 mM, and a pH is 6.5-8.5; a DNA sequence of $Y_{0a}$ is shown as SEQ ID NO.1: CCTGTCTGCCTAATGTGCGTCGTAAG; a DNA sequence of $Y_{0b}$ is shown as SEQ ID NO.2: CTTACGACGCACAAGGAGATCATGAG; and a DNA sequence of $Y_{0c}$ is shown as SEQ ID NO.3: CTCATGATCTCCTTTAGGCAGACAGG.

In an embodiment of the disclosure, the template strand Y-shaped DNA solution in step (1) is diluted with an MOPS buffer and has a concentration of 2 μM. The ascorbic acid solution and the cupric acetate solution are prepared and diluted with ultrapure water (18.2 MΩ.cm). The ascorbic acid solution has a concentration of 1.25 mM, and the cupric acetate solution has a concentration of 0.05-2 mM. A volume ratio of the template strand Y-shaped DNA solution to the ascorbic acid solution to the cupric acetate solution is 5:5:2.

In an embodiment of the disclosure, the DNA-Cu NMs in step (1) is only mixed 1-20 min after synthesis.

In an embodiment of the disclosure, the β-CD solution in step (2) is prepared and diluted with ultrapure water (18.2 MΩ·cm) and has a concentration of 0.5-5 mM.

In an embodiment of the disclosure, a volume ratio of the DNA-Cu NMs solution to the β-CD solution in step (2) is 900:133.

In an embodiment of the disclosure, the ultrafiltration in step (2) is ultrafiltration through a 10 kd ultrafiltration tube.

In an embodiment of the disclosure, the β-CD@DNA-Cu NMs obtained in step (2) are stored at 4° C. in the dark.

A second object of the disclosure is to provide fluorescent copper nanoparticles β-CD@DNA-Cu NMs prepared by the method according to the disclosure.

A third object of the disclosure is to provide a method for preparing a β-CD@DNA-Cu NMs-AFB1 ratiometric fluorescent sensor, including the following steps:

adding a solution of β-CD@DNA-Cu NMs to an AFB1 solution, shaking the mixture at 300-500 rpm for 0.5-1.5 min, and mixing the mixture uniformly to obtain the β-CD@DNA-Cu NMs-AFB1 ratiometric fluorescent sensor.

In an embodiment of the disclosure, a volume ratio of the solution of β-CD@DNA-Cu NMs to the AFB1 solution is 1:8-10, further preferably 1:9. The AFB1 solution is obtained by dissolving AFB1 in 1-40% methanol/water (V/V %).

In an embodiment of the disclosure, a concentration of the β-CD@DNA-Cu NMs is 200 μM-2 mM, and the AFB1 solution has a concentration of 0.05-18 ppb.

A fourth object of the disclosure is to provide a β-CD@DNA-Cu NMs-AFB1 ratiometric fluorescent sensor prepared by the method according to the disclosure.

A fifth object of the disclosure is to provide a method for preparing a β-CD@DNA-Cu NMs-M-AFB1 ratiometric fluorescent sensor with metal ions M as a fluorescence enhancer of AFB1, including the following steps:

mixing an AFB1 solution and a metal ions M solution uniformly to obtain an M-AFB1 mixed solution; and then adding a solution of β-CD@DNA-Cu NMs to the M-AFB1 mixed solution, shaking the mixture at 300-500 rpm for 0.5-1.5 min, and mixing the mixture uniformly to obtain the β-CD@DNA-Cu NMs-M-AFB1 ratiometric fluorescent sensor.

In an embodiment of the disclosure, the AFB1 solution has a concentration of 0.05-18 ppb, and uses a methanol solution with a volume fraction of 40% as a solvent. Further preferably, the AFB1 solution has a concentration of 10 ppb.

In an embodiment of the disclosure, the metal ions M solution has a concentration of 1-50 mM, and uses a methanol solution with a volume fraction of 40% as a solvent.

In an embodiment of the disclosure, the metal ions M include: platinum ions ($Pt^{2+}$), ytterbium ions ($Yb^{3+}$), erbium ions ($Er^{3+}$), yttrium ions ($Y^{3+}$), calcium ions ($Ca^{2+}$) and mercury ions ($Hg^{2+}$).

In an embodiment of the disclosure, metal compounds corresponding to the metal ions M include: tetrachloroplatinic acid ($K_2PtCl_4$), ytterbium chloride hexahydrate ($YbCl_3 \cdot 6H_2O$), erbium chloride ($ErCl_3$), yttrium chloride hexahydrate ($YCl_3 \cdot 6H_2O$), anhydrous calcium chloride ($CaCl_2$) and an $Hg^{2+}$ standard solution.

In an embodiment of the disclosure, a volume ratio of the AFB1 solution to the metal ions M solution is 7-9:1, further preferably 8:1.

In an embodiment of the disclosure, the solution of β-CD@DNA-Cu NMs is obtained by dispersing β-CD@DNA-Cu NMs in a methanol solution with a volume fraction of 40%.

In an embodiment of the disclosure, a volume ratio of the solution of β-CD@DNA-Cu NMs to the M-AFB1 mixed solution is 1:9.

In an embodiment of the disclosure, the shaking is shaking in a mixer at 400 rpm for 1 min.

A sixth object of the disclosure is to provide a β-CD@DNA-Cu NMs-M-AFB1 ratiometric fluorescent sensor with metal ions M as a fluorescence enhancer of AFB1 prepared by the method according to the disclosure.

A seventh object of the disclosure is to provide a method for detecting AFB1 based on the β-CD@DNA-Cu NMs-M-AFB1 ratiometric fluorescent sensor with metal ions M as a fluorescence enhancer of AFB1, including the following steps:

(1) pretreatment of sample:

adding an extraction solvent to a sample to be tested to carry out extraction, and carrying out centrifugation and filtration to obtain a sample to be analyzed; and (2) testing:

carrying out fluorescence detection on the sample to be analyzed to obtain fluorescence values at 433 nm and 650 nm, $I_{433}$ nm and $I_{650}$ nm, and then substituting the fluorescence values into an AFB1 standard curve to obtain a concentration of AFB1 in the sample to be tested.

In an embodiment of the disclosure, the extraction solvent in step (1) is one of methanol/water, ethanol/water or acetonitrile/water with a volume fraction of 40%.

In an embodiment of the disclosure, a ratio of the sample to be tested to the extraction solvent in step (1) is 1:3-5 in g/mL, further preferably 1:4.

In an embodiment of the disclosure, the extraction in step (1) is extraction in a shaker at a speed of 250 rpm for 30 min, followed by ultrasonic treatment for 10 min; the centrifugation is centrifugation at a speed of 10000 r/min for 5 min; and the filtration is filtration of the supernatant through a 0.22 μm filter membrane.

In an embodiment of the disclosure, before the detection in step (2), the sample to be analyzed needs to be appropriately diluted 2-10 times according to the type of the sample, in order to reduce the interference of other matrices in the detection of AFB1.

In an embodiment of the disclosure, the fluorescence detection in step (2) is carried out under an excitation bandwidth of 10 nm, a slit width of 10 nm and an excitation wavelength of 365 nm, and fluorescence values at emission peaks 433 nm (AFB1) and 650 nm (β-CD@DNA-Cu NMs) are detected.

In an embodiment of the disclosure, the AFB1 standard curve in step (2) is $I_{433}$ nm/$I_{650}$ nm=0.0627C−0.0068, $R^2$=0.9963, and a linear range is 0.03-10 ppb; and $I_{433}$ nm/$I_{650}$ nm=0.4825C−4.7038, $R^2$=0.9736, a linear range is 10-18 ppb, and a limit of detection is 0.012 ppb (S/N=3), where $I_{433}$ nm is the maximum fluorescence value of AFB1, $I_{650}$ nm is the maximum fluorescence value of β-CD@DNA-Cu NMs, and the ratio value of $I_{433}$ nm/$I_{650}$ nm represents the detection result; and C is the concentration of AFB1.

An eighth object of the disclosure is to provide use of the fluorescent copper nanoparticles β-CD@DNA-Cu NMs, the β-CD@DNA-Cu NMs-AFB1 ratiometric fluorescent sensor and the β-CD@DNA-Cu NMs-M-AFB1 ratiometric fluorescent sensor with metal ions M as a fluorescence enhancer of AFB1 according to the disclosure in detection of a food toxin.

In an embodiment of the disclosure, the toxin includes aflatoxin B1.

A ninth object of the disclosure is to provide use of the method for detecting AFB1 based on the β-CD@DNA-Cu NMs-M-AFB1 ratiometric fluorescent sensor with metal ions M as a fluorescence enhancer of AFB1 according to the disclosure in detection of a food toxin.

In an embodiment of the disclosure, the toxin includes aflatoxin B1.

In an embodiment of the disclosure, the use is detection of aflatoxin B1 in grains.

In an embodiment of the disclosure, the grains include rice, wheat, corn, barley and millet.

Beneficial Effects (1) In the disclosure, the fluorescent copper nanoparticless (β-CD@DNA-Cu NMs) with high fluorescence and high stability are prepared, and the method for detecting AFB1 based on the β-CD@DNA-Cu NMs ratiometric fluorescent sensor is established. The detection method of the disclosure achieves detection of AFB1 with high sensitivity (the limit of detection is 0.012 ppb), high speed (1 min), no toxicity or low toxicity and high specificity.

(2) The method for detecting AFB1 based on β-CD@DNA-Cu NMs-M-AFB1 according to the disclosure achieves highly sensitive fluorescence detection of AFB1. Compared with the ratiometric fluorescence detection method based on β-CD@DNA-Cu NMs-AFB1 in the disclosure, the ratiometric fluorescence detection method based on β-CD@DNA-Cu NMs-$Ca^{2+}$-AFB1 increases the sensitivity for AFB1 by 22 times. Moreover, according to this method, in the ranges of 0.05-10 ppb and 10-18 ppb, the ratio value of $I_{433}$ nm/$I_{650}$ nm and the concentration of AFB1 exhibit a good linear relationship respectively, and the limit of detection is 0.012 ppb.

(3) The method for detecting AFB1 according to the disclosure has high selectivity, and other mycotoxins will not interfere with the determination of AFB1. Generally, when other common mycotoxins (AFB2, AFG1, AFG2, T-2, AFM1, ZEN and OTA) in the grain sample are added at a concentration of 500 ppb, the fluorescence is enhanced by less than 4 times. In contrast, when the AFB1 is added at a concentration of 10 ppb, the fluorescence is enhanced by 22 times.

(4) The method for detecting AFB1 according to the disclosure can achieve detection with no toxicity or low toxicity. Low concentrations of $Pt^{2+}$, $Yb^{3+}$, $Er^{3+}$ and $Y^{3+}$ serving as the fluorescence enhancer can enhance the sensitivity of the β-CD@DNA-Cu NMs-AFB1 ratiometric fluorescent sensor by 9.67-22.13 times, and can achieve detection with low toxicity as compared with $Hg^{2+}$. A high concentration of $Ca^{2+}$ can also improve the detection result of AFB1 and enhance the sensitivity by 22 times, and $Ca^{2+}$ is nontoxic and cheap.

(5) The method of the disclosure has the advantages including high sensitivity, high selectivity, fast detection, and no toxicity or low toxicity.

(6) The detection principle of the disclosure is as follows:

Firstly, in the disclosure, the β-CD@DNA-Cu NMs are synthesized by using the Y-shaped DNA (Y-shaped complementary nucleic acid duplex) as the template, the ascorbic acid (AA) as the reducing agent and the mono-(6-mercapto-6-deoxy)-β-cyclodextrin (β-CD) as the fluorescence stabilizing and enhancing agent. Secondly, in the disclosure, the ratiometric fluorescent probe is constructed based on the β-CD@DNA-Cu NMs. The β-CD can enhance and stabilize the fluorescence of the β-CD@DNA-Cu NMs. Moreover, due to the host-guest interaction between β-CD and AFB1, the β-CD@DNA-Cu NMs-AFB1 complex can be formed. The above process can enhance the fluorescence of AFB1. Since the ultraviolet absorption spectrum of AFB1 overlaps the fluorescence excitation spectrum of β-CD@DNA-Cu NMs, an inner filter effect (IFE) occurs, which leads to the fluorescence quenching of the β-CD@DNA-Cu NMs. Finally, according to the disclosure, it is found that the metal ions including $Pt^{2+}$, $Yb^{3+}$, $Er^{3+}$ and $Y^{3+}$ can further enhance the fluorescence of AFB1 in the above system, thereby enhancing the sensitivity of ratiometric fluorescence detection of AFB1.

DETAILED DESCRIPTION

Preferred examples of the disclosure will be described below. It should be understood that the examples are intended to better explain the disclosure and are not intended to limit the disclosure.

Example 1

A method for preparing fluorescent copper nanoparticles β-CD@DNA-Cu NMs included the following steps:

(1) Preparation of template strand Y-shaped complementary nucleic acid duplex (Y-shaped DNA):

Three oligonucleotide strands ($Y_{0a}$, $Y_{0b}$, $Y_{0c}$) (Table 1) were equally mixed in an MOPS buffer (10 mM, pH 7.5, 150 mM NaAc, 1 mM $MgCl_2$) to obtain a mixed solution. Then the mixed solution was heated to 90° C., and after 5 min of denaturation, the mixed solution was slowly cooled to room temperature to obtain the Y-shaped DNA. The Y-shaped DNA solution was stored in a refrigerator at −18° C.

TABLE 1

DNA sequences of oligonucleotide strands

| No. | Sequence (from 5' to 3') | |
|---|---|---|
| $Y_{0a}$ | CCTGTCTGCCTAATGTGCGTCGTAAG | SEQ ID NO. 1 |
| $Y_{0b}$ | CTTACGACGCACAAGGAGATCATGAG | SEQ ID NO. 2 |
| $Y_{0c}$ | CTCATGATCTCCTTTAGGCAGACAGG | SEQ ID NO. 3 |

(2) Preparation of DNA-Cu NMs:

The Y-shaped DNA solution (500 μL, 2 μM) and an ascorbic acid solution (500 μL, 1.25 mM) were mixed, then a cupric acetate solution (200 μL, 2 mM) was added, and the mixture was mixed thoroughly for 20 min until the solution turned yellow, thereby obtaining a DNA-Cu NMs solution.

Figure 1:
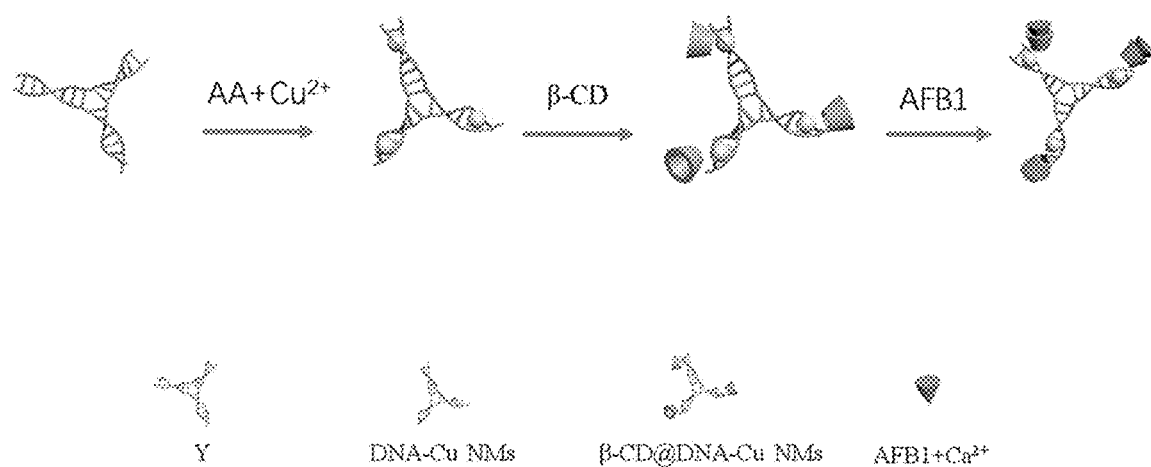
FIG. 1 is a schematic diagram of detection of AFB1 by a β-CD@DNA-Cu NMs-AFB1 ratiometric fluorescent sensor.

(3) β-CD modified DNA-Cu NMs:

900 μL of the DNA-Cu NMs solution and 133 μL of β-CD (2 mM) were mixed thoroughly for 1 min until the mixed solution turned from yellow to colorless. Then the excess reagents were removed by ultrafiltration through a 10 kd ultrafiltration tube to obtain β-CD@DNA-Cu NMs, which were stored at 4° C. in the dark. A schematic diagram of synthesis of β-CD@DNA-Cu NMs is shown in FIG. 1.

The Y-shaped DNA solution was prepared and diluted with an MOPS buffer (10 mM, pH 7.5, 150 mM NaAc, 1 mM $MgCl_2$). The ascorbic acid solution, the cupric acetate solution and the β-CD solution were prepared and diluted with ultrapure water (18.2 MΩ·cm).

Example 2 Optimization of Preparation Process of Fluorescent Copper Nanoparticles The concentrations of the β-CD solution in Example 1 were adjusted to 0.5 mM, 2 mM and 5 mM, and the others conditions were the same as those in Example 1, thereby obtaining β-CD@DNA-Cu NMs.

Figure 2A:
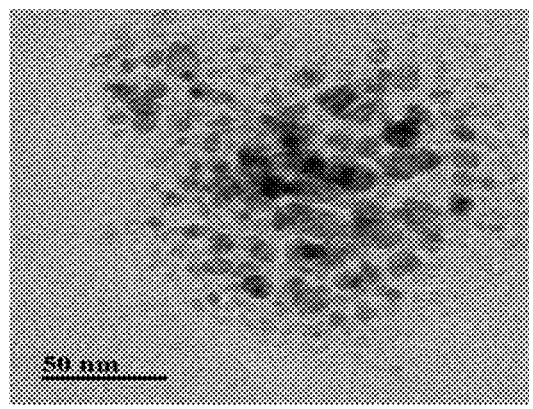
FIG. 2A shows TEM images of β-CD@DNA-Cu NMs modified with β-CD at 0.5 mM.
Figure 2B:
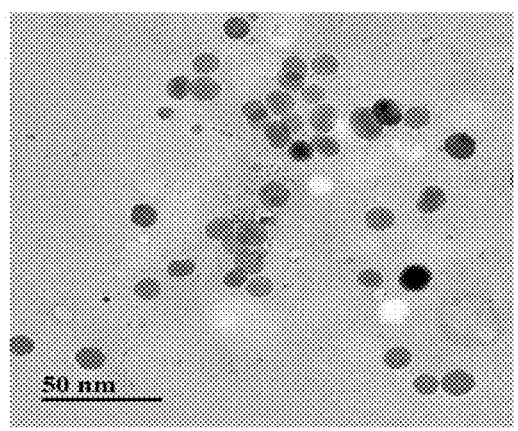
FIG. 2B shows TEM images of β-CD@DNA-Cu NMs modified with β-CD at 2 mM.
Figure 2C:
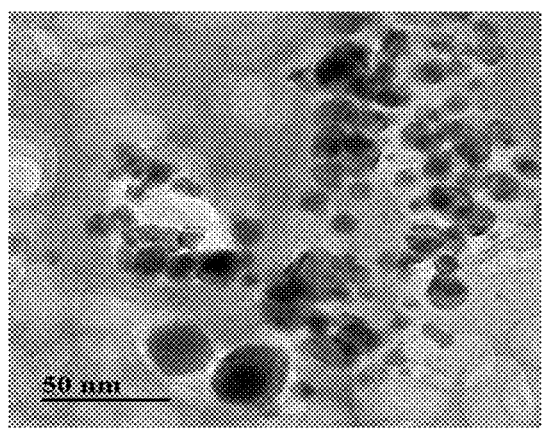
FIG. 2C shows TEM images of β-CD@DNA-Cu NMs modified with β-CD at 5 mM.

The obtained β-CD@DNA-Cu NMs were subjected to fluorescence testing under an excitation bandwidth of 10 nm, a slit width of 10 nm and an excitation wavelength of 365 nm. The test results are as follows:

FIG. 2A, FIG. 2B and FIG. 2C shows TEM images of β-CD@DNA-Cu NMs modified with β-CD at different concentrations. As can be seen from FIG. 2A, FIG. 2B and FIG. 2C, as the concentration of β-CD increased from 0.5 mM to 2 mM and 5 mM, the average sizes of the β-CD@DNA-Cu NMs respectively increased from 10 nm to 12 nm and 14 nm. When the concentration of β-CD was in the range of 0-5 mM, with the increase of its concentration, the fluorescence became stronger. The fluorescence enhancement was associated with the stability of β-CD to copper nanoparticles. From the aspect of characterization, as the concentration of β-CD increased, the particle size increased, which was due to the increase in the quantity of β-CD modified copper nanoparticles.

Figure 3:
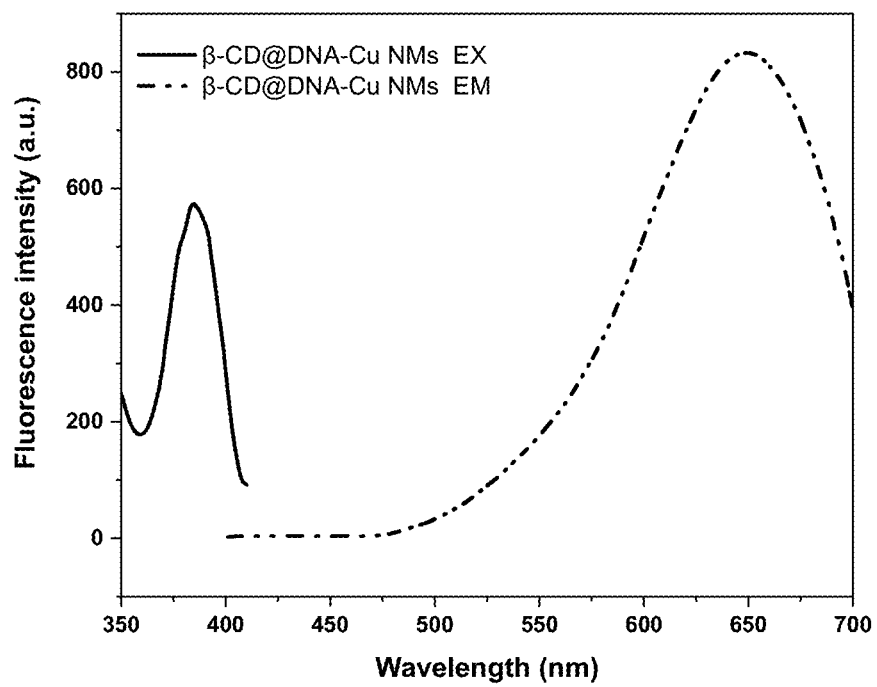
FIG. 3 shows a fluorescence excitation spectrum (Ex) and an emission spectrum (Em) of β-CD@DNA-Cu NMs.
Figure 4A:
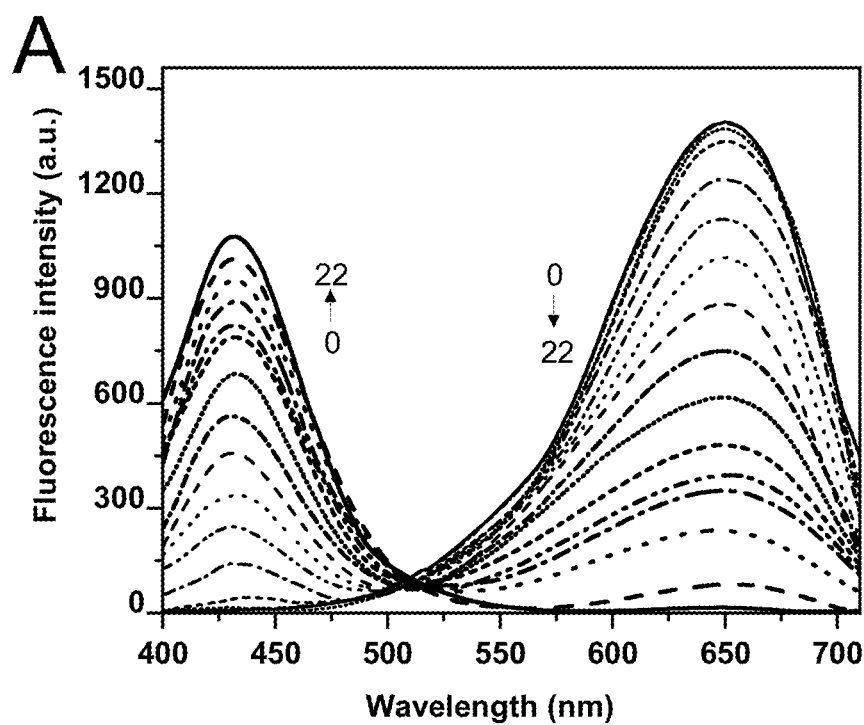
FIG. 4A shows ratiometric fluorescent curves of β-CD@DNA-Cu NMs-$Ca^{2+}$-AFB1 when different concentrations of AFB1 are added.
Figure 4B:
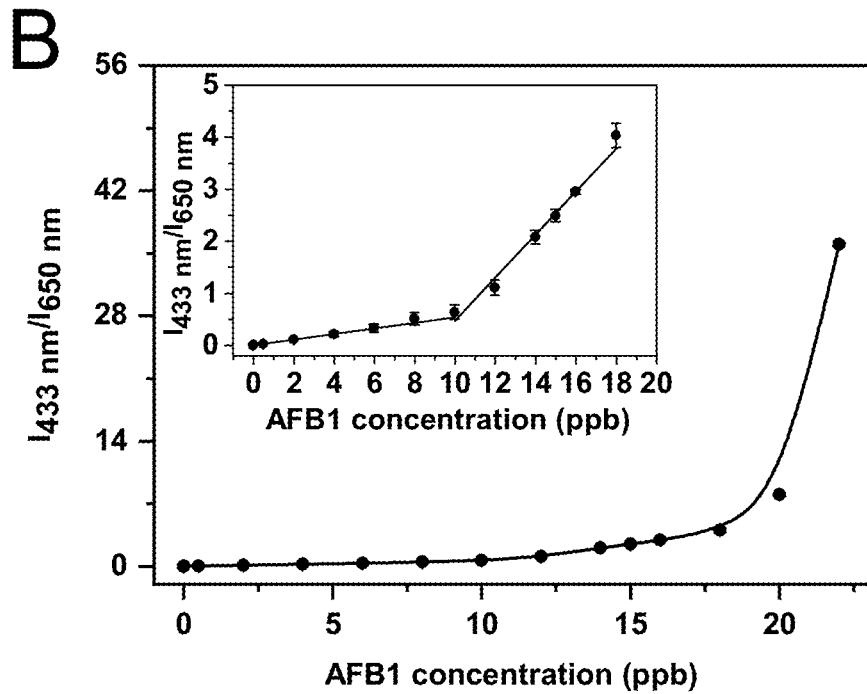
FIG. 4B shows standard curves of β-CD@DNA-Cu NMs-$Ca^{2+}$-AFB1 when different concentrations of AFB1 are added.

A fluorescence excitation spectrum (Ex) and an emission spectrum (Em) of β-CD@DNA-Cu NMs are shown in FIG. 3. The β-CD modified β-CD@DNA-Cu NMs at 2 mM exhibited spherical particles with uniform particle size and good dispersion, and had an average particle size of 12 nm, thus being the best. The fluorescence excitation wavelength of the β-CD@DNA-Cu NMs was in the range of 358-410 nm. When the excitation wavelength was between 358 nm and 410 nm, the emission peak of the β-CD@DNA-Cu NMs was not affected. Therefore, in order to obtain the maximum AFB1 fluorescence signal, 365 nm was selected as the excitation wavelength of the β-CD@DNA-Cu NMs-AFB1 or the β-CD@DNA-Cu NMs-M-AFB1 ratiometric system.

Example 3

A method for preparing a β-CD@DNA-Cu NMs-AFB1 ratiometric fluorescent sensor included the following steps:

The solution of β-CD@DNA-Cu NMs (100 μL, 200 μM) obtained in Example 1 was added to an AFB1 solution (900 μL, 10 ppb), the mixture was shaken at 400 rpm for 1 min, and the mixture was mixed uniformly to obtain the β-CD@DNA-Cu NMs-AFB1 ratiometric fluorescent sensor.

The obtained β-CD@DNA-Cu NMs-AFB1 ratiometric fluorescent sensor was subjected to fluorescence testing under an excitation bandwidth of 10 nm, a slit width of 10 nm and an excitation wavelength of 365 nm. Fluorescence values at emission peaks 433 nm (AFB1) and 650 nm (β-CD@DNA-Cu NMs) were detected.

Example 4

A method for preparing a β-CD@DNA-Cu NMs-M-AFB1 ratiometric fluorescent sensor with metal ions M as a fluorescence enhancer of AFB1 included the following steps:

(1) An AFB1 standard solution was diluted to 10 ppb with methanol/water with a volume fraction of 40%. The β-CD@DNA-Cu NMs prepared in Example 1 were diluted to 200 μM with methanol/water with a volume fraction of 40%. A metal ions M solution was diluted with methanol/water with a volume fraction of 40%.

(2) 800 μL of AFB1 solution and 100 μL of metal ions M solution (the concentrations are shown in Table 2) were mixed to obtain an M-AFB1 mixed solution. Then, 100 μL of solution of β-CD@DNA-Cu NMs was added to 900 μL of M-AFB1 mixed solution, and the mixture was shaken at 400 rpm for 1 min to obtain the β-CD@DNA-Cu NMs-M-AFB1 ratiometric fluorescent sensor with metal ions M as a fluorescence enhancer of AFB1.

The metal ions M include: platinum ions ($Pt^{2+}$), palladium ions ($Pd^{2+}$), ytterbium ions ($Yb^{3+}$), erbium ions ($Er^{3+}$), yttrium ions ($Y^{3+}$), magnesium ions ($Mg^{2+}$), thulium ions ($Tm^{3+}$), calcium ions ($Ca^{2+}$), mercury ions ($Hg^{2+}$), potassium ions ($K^+$), sodium ions ($Na^+$), aluminum ions ($Al^{3+}$) and copper ions ($Cu^{2+}$). Metal compounds used were: tetrachloroplatinic acid ($K_2PtCl_4$), anhydrous palladium chloride (PdCl$_2$), ytterbium chloride hexahydrate (YbCl$_3$·6H$_2$O), erbium chloride (ErCl$_3$), yttrium chloride hexahydrate (YCl$_3$·6H$_2$O), magnesium chloride hexahydrate (MgCl$_2$·6H$_2$O), thulium chloride hexahydrate (TmCl$_3$·6H$_2$O), anhydrous calcium chloride (CaCl$_2$), an Hg$^{2+}$ standard solution, potassium chloride (KCl), sodium chloride (NaCl), aluminum chloride (AlCl$_3$) and cupric chloride (CuCl$_2$).

The obtained β-CD@DNA-Cu NMs-M-AFB1 ratiometric fluorescent sensor with metal ions M as a fluorescence enhancer of AFB1 was subjected to fluorescence spectrum detection by using a fluorophotometer under an excitation bandwidth of 10 nm, a slit width of 10 nm and an excitation wavelength of 365 nm. Fluorescence values at emission peaks 433 nm (AFB1) and 650 nm (β-CD@DNA-Cu NMs) were detected.

The test results are shown in Table 2:

TABLE 2

Effects of different metal ions on fluorescence of β-CD@DNA-Cu NMs-M-AFB1 system.

| Metal ions M | Concentration of metal ions M (mmol/L) | $F_C$-$F_M$ | ($F_C$-$F_M$)/$F_{AFB1}$ |
|---|---|---|---|
| $Pt^{2+}$ | 1 mM | 554.5 | 22.13 |
| $Pd^{2+}$ | 1 mM | 30 | 1.03 |
| $Yb^{3+}$ | 1 mM | 485.5 | 18.67 |
| $Er^{3+}$ | 1 mM | 479.8 | 18.51 |
| $Y^{3+}$ | 1 mM | 251.3 | 9.67 |
| $Hg^{2+}$ | 1 mM | 425.7 | 16.37 |
| $Ca^{2+}$ | 50 mM | 551.24 | 22 |
| $Tm^{3+}$ | 5 mM | 18.6 | 0.72 |
| $Mg^{2+}$ | 5 mM | 28.1 | 1.08 |
| $K^+$ | 5 mM | 28.5 | 1.09 |
| $Cu^{2+}$ | 5 mM | 26.1 | 1 |
| $Al^{3+}$ | 5 mM | 26.3 | 1.01 |
| $Na^+$ | 5 mM | 26.9 | 1 |

NOTE:

$F_C$ is the fluorescence intensity of β-CD@DNA-Cu NMs-M-AFB1 at 433 nm;

M represents different metal ions;

$F_M$ is the background fluorescence of different metal ions at 433 nm;

$F_{AFB1}$ is the fluorescence value of 10 ppb AFB1;

and ($F_C$-$F_M$)/$F_{AFB1}$ is the number of times of fluorescence enhancement of AFB1 caused by different metal ions in the β-CD@DNA-Cu NMs-M-AFB1 system at 433 nm.

As can be seen from Table 2, 1 mM $Pt^{2+}$, $Yb^{3+}$, $Er^{3+}$ and $Y^{3+}$ could enhance the ($F_C$−$F_M$)/$F_{AFB1}$ value of AFB1 by 9.67-22.13 times. Under the condition of the same concentration, compared with the detection effect of $Hg^{2+}$, $Pt^{2+}$, $Yb^{3+}$, $Er^{3+}$ and $Y^{3+}$ in the traditional method on AFB1, this example could achieve similar enhancement effect with much lower toxicity. 50 mM $Ca^{2+}$ could enhance the ($F_C$−$F_M$)/$F_{AFB1}$ value of AFB1 by 22 times, and $Ca^{2+}$ was nontoxic and could be better used in practical detection.

Example 5

A method for detecting AFB1 based on a β-CD@DNA-Cu NMs-M-AFB1 ratiometric fluorescent sensor with metal ions M as a fluorescence enhancer of AFB1 included the following steps:

(1) Creation of standard curve

An AFB1 standard solution was diluted with methanol/water with a volume fraction of 40% to 0 ppb, 0.05 ppb, 2 ppb, 4 ppb, 6 ppb, 8 ppb, 10 ppb, 12 ppb, 14 ppb, 16 ppb and 18 ppb respectively. The β-CD@DNA-Cu NMs prepared in Example 1 were diluted to 200 μM with methanol/water with a volume fraction of 40%. A $Ca^{2+}$ solution was diluted to 50 mM with methanol/water with a volume fraction of 40%.

800 μL of AFB1 solution at different concentrations was mixed with 100 μL of $CaCl_2$ solution (50 mM) to obtain a $Ca^{2+}$-AFB1 mixed solution. Then, 100 μL of solution of β-CD@DNA-Cu NMs was added to 900 μL of $Ca^{2+}$-AFB1 mixed solution, and the mixture was shaken at 400 rpm for 1 min.

By using a fluorophotometer, under an excitation bandwidth of 10 nm, a slit width of 10 nm and an excitation wavelength of 365 nm, fluorescence values at emission peaks 433 nm (AFB1) and 650 nm (β-CD@DNA-Cu NMs) were detected.

A standard curve was created based on the obtained $I_{433}$ nm/$I_{650}$ nm and the concentration of AFB1:

The AFB1 standard curve is shown in 4. The standard curve was $I_{433}$ nm/$I_{650}$ nm=0.0627C−0.0068, $R^2$=0.9963, and a linear range was 0.03-10 ppb; and $I_{433}$ nm/$I_{650}$ nm=0.4825C−4.7038, $R^2$=0.9736, a linear range was 10-18 ppb, and a limit of detection was 0.012 ppb (S/N=3). $I_{433}$ nm was the maximum fluorescence value of AFB1, and $I_{650}$ nm was the maximum fluorescence value of β-CD@DNA-Cu NMs. The ratio value of $I_{433}$ nm/$I_{650}$ nm represented the detection result. C was the concentration of AFB1.

(2) Pretreatment of samples:

AFB1 standards at concentrations of 0.5 ppb, 10 ppb and 15 ppb were respectively added to rice samples. After being dried, the samples were placed at room temperature in the dark for 2 d. Then the rice samples were finely ground to powder, which served as samples to be tested.

5.0 g of sample to be tested was accurately weighed in a 50.0 mL centrifuge tube, and 20 mL of methanol/water with a volume percentage of 40% was added. The mixture was extracted by being shaken in a shaker at a speed of 250 rpm for 30 min and then subjected to ultrasonic treatment for 10 min for extraction. After the completion of the extraction, centrifugation was carried out at a speed of 10000 r/min for 5 min, thereby obtaining a supernatant. Then, the supernatant was filtered through a 0.22 μm filter membrane to obtain a sample to be analyzed. The sample to be analyzed was stored at 4° C.

(3) Testing:

Before analysis, the sample to be analyzed was pre-diluted 10 times. Then fluorescent testing was carried out under an excitation bandwidth of 10 nm, a slit width of 10 nm and an excitation wavelength of 365 nm, and fluorescence values at emission peaks 433 nm (AFB1) and 650 nm (β-CD@DNA-Cu NMs) were detected.

Example 6 Accuracy and Specificity of Method of Example 5

1. Accuracy of Method

AFB1 standard solutions at concentrations of 0.05 ppb, 10 ppb and 15 ppb were respectively added to rice samples, and then testing was carried out by using the β-CD@DNA-Cu NMs-M-AFB1 ratiometric fluorescent sensor with metal ions $Ca^{2+}$ as a fluorescence enhancer of AFB1 in Example 4. Each sample was tested 3 times. For specific operations, reference is made to Example 5.

The test results are shown in Table 3. As can be seen from Table 3, the average concentrations of AFB1 were respectively 0.049 ppb, 9.62 ppb and 15.207 ppb, the recoveries were 96.2%-101%, and the relative standard deviation (RSD) values were all less than 3.5%, indicating that the method had good accuracy and precision.

TABLE 3

Determination of AFB1 in grain (rice) samples (n = 3)

| Sample | Added (ppb) | Found (ppb) | Recovery (%) | RSD (%) |
|---|---|---|---|---|
| Rice sample | 0.05 | 0.049 | 98 | 2.81 |
|  | 10 | 9.62 | 96.2 | 3.03 |
|  | 15 | 15.207 | 101.4 | 3.42 |

2. Specificity of Method: Effects of Common Toxins in Rice Samples on Detection Ratiometric fluorescent probes were constructed from different toxins and β-CD@DNA-Cu NMs and used to detect AFB1. The specific operations are as follows:

800 μL of different toxins (500 ppb, namely AFB2, AFG1, AFG2, T-2, AFM1, ZEN and OTA) or 800 μL of different toxins (500 ppb) mixed with aflatoxin B1 (10 ppb) was mixed with 100 μL of $CaCl_2$ solution (50 mM) to obtain a mixed solution. Then 100 μL of solution of β-CD@DNA-Cu NMs (200 μM) was taken and added to 900 μL of mixed solution, and the resulting mixture was shaken at 400 rpm for 1 min. Finally, fluorescence testing was carried out. Each sample was tested 3 times.

Figure 5A:
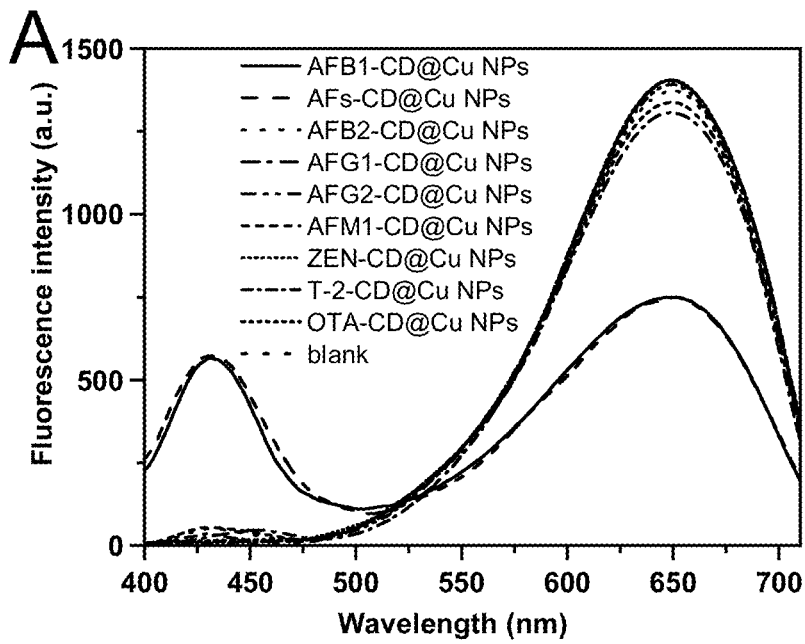
FIG. 5A shows fluorescence spectra when other toxins in the grain sample (rice) are detected by the β-CD@DNA-Cu NMs-M-AFB1.
Figure 5B:
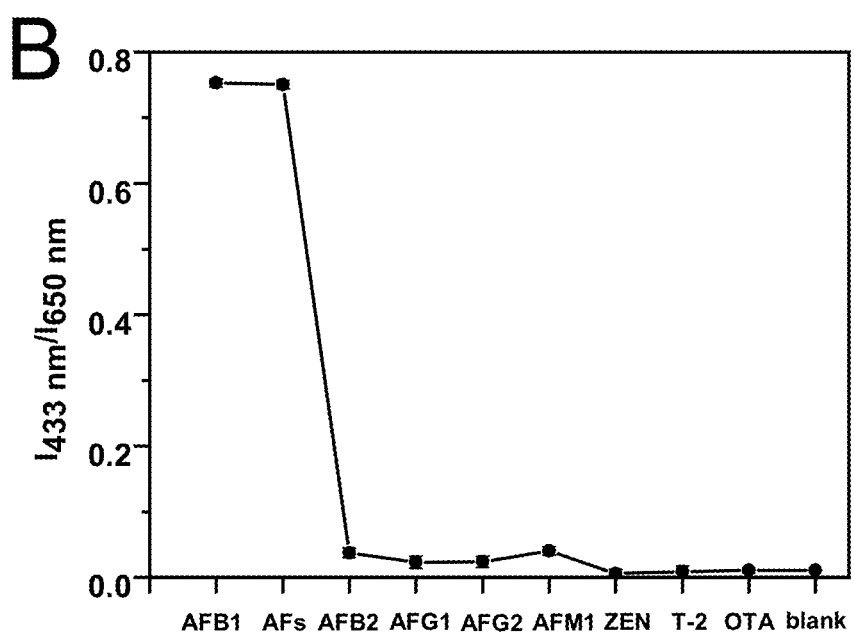
FIG. 5B shows the ratio value of $I_{433}$ nm/$I_{650}$ nm when other toxins in the grain sample (rice) are detected by the β-CD@DNA-Cu NMs-M-AFB1.

The results are shown in FIG. 5A and FIG. 5B. As can be seen from FIG. 5A and FIG. 5B, when other common toxins (AFB2, AFG1, AFG2, T-2, AFM1, ZEN and OTA) were added at a concentration of 500 ppb, the fluorescence was enhanced by less than 4 times. In contrast, when the AFB1 was added at a concentration of 10 ppb, the fluorescence was enhanced by 22 times. The results demonstrated that these other common toxins could not interfere with the detection results of AFB1.

Example 7

The $CaCl_2$ solution (50 mM) in Example 5 may be replaced with $K_2PtCl_4$ (1 mM), $YbCl_3 \cdot 6H_2O$ (1 mM), $ErCl_3$ (1 mM) and $YCl_3 \cdot 6H_2O$ (1 mM), which were also suitable for detecting AFB1 in rice.

---

What is claimed is:

1. A method for preparing fluorescent copper nanoparticles β-CD@DNA-Cu NMs, comprising the following steps:
   (1) preparing of DNA-Cu NMs by
   mixing a template strand Y-shaped DNA solution and an ascorbic acid solution uniformly, then adding a cupric acetate solution, and mixing the mixture uniformly to obtain a DNA-Cu NMs solution; and
   (2) preparing of β-CD modified DNA-Cu NMs by
   mixing the DNA-Cu NMs solution obtained in step (1) and a β-CD solution uniformly, and performing ultrafiltration to obtain the β-CD@DNA-Cu NMs.

2. The method according to claim 1, wherein the β-CD solution in step (2) has a concentration of 0.5-5 mM.

3. The method according to claim 1, wherein further comprising preparing the template strand Y-shaped DNA in step (1) by:
   mixing three oligonucleotide strands ($Y_{0a}$, $Y_{0b}$, $Y_{0c}$) equally in an MOPS buffer to obtain a mixed solution; then heating the mixed solution to 90° C., and after 5 min of denaturation, slowly cooling the mixed solution to room temperature to obtain the Y-shaped DNA; and storing the Y-shaped DNA solution in a refrigerator at −18° C., wherein the MOPS buffer has a concentration of 5-20 mM, a concentration of NaAc is 75-300 mM, a concentration of $MgCl_2$ is 1-10 mM, and a pH is 6.5-8.5; a DNA sequence of $Y_{0a}$ is set forth in SEQ ID NO.1: CCTGTCTGCCTAATGTGCGTCGTAAG; a DNA sequence of $Y_{0b}$ is set forth in SEQ ID NO.2: CTTACGACGCACAAGGAGATCATGAG; and a DNA sequence of $Y_{0c}$ is set forth SEQ ID NO.3: CTCATGATCTCCTTTAGGCAGACAGG.

4. A method for preparing a β-CD@DNA-Cu NMs-AFB1 ratiometric fluorescent sensor based on the fluorescent copper nanoparticles β-CD@DNA-Cu NMs prepared by the method according to claim 1, comprising the following steps:
   adding a solution of the fluorescent copper nanoparticles β-CD@DNA-Cu NMs prepared by the method according to claim 1 to an AFB1 solution, shaking the mixture at 300-500 rpm for 0.5-1.5 min, and mixing the mixture uniformly to obtain the β-CD@DNA-Cu NMs-AFB1 ratiometric fluorescent sensor, wherein a concentration of the β-CD@DNA-Cu NMs is 200 μM-2 mM, and the AFB1 solution has a concentration of 0.05-18 ppb.

5. The method according to claim 4, wherein a volume ratio of the solution of β-CD@DNA-Cu NMs to the AFB1 solution is 1:8-10.

6. The method according to claim 4, wherein the AFB1 solution is obtained by dissolving AFB1 in 1-40% methanol/water (V/V).

7. A method for preparing a β-CD@DNA-Cu NMs-M-AFB1 ratiometric fluorescent sensor with metal ions M as a fluorescence enhancer of AFB1 based on the β-CD@DNA-Cu NMs-AFB1 ratiometric fluorescent sensor prepared by the method according to claim 4, comprising the following steps:
   mixing an AFB1 solution and a metal ions M solution uniformly to obtain an M-AFB1 mixed solution; and then adding a solution of the fluorescent copper nanoparticles β-CD@DNA-Cu NMs prepared by the method according to claim 1 to the M-AFB1 mixed solution, shaking the mixture at 300-500 rpm for 0.5-1.5 min, and mixing the mixture uniformly to obtain the β-CD@DNA-Cu NMs-M-AFB1 ratiometric fluorescent sensor.

8. The method according to claim 7, wherein the AFB1 solution has a concentration of 0.05-18 ppb, the metal ions M solution has a concentration of 1-50 mM, and the metal ions M comprise $Pt^{2+}$, $Yb^{3+}$, $Er^{3+}$, $Y^{3+}$, $Ca^{2+}$ and $Hg^{2+}$.

9. The method according to claim 7, wherein metal compounds corresponding to the metal ions M comprise: tetrachloroplatinic acid, ytterbium chloride hexahydrate, erbium chloride, yttrium chloride hexahydrate, anhydrous calcium chloride and an $Hg^{2+}$ standard solution.

10. The method according to claim 7, wherein a volume ratio of the AFB1 solution to the metal ions M solution is 7-9:1.

11. The method according to claim 7, wherein a volume ratio of the solution of β-CD@DNA-Cu NMs to the M-AFB1 mixed solution is 1:9.

12. A β-CD@DNA-Cu NMs-M-AFB1 ratiometric fluorescent sensor with metal ions M as a fluorescence enhancer of AFB1 prepared by the method according to claim 7.

13. A method for detecting AFB1 based on the β-CD@DNA-Cu NMs-M-AFB1 ratiometric fluorescent sensor with metal ions M as a fluorescence enhancer of AFB1 according to claim 12, comprising the following steps:
   (1) pretreatment of sample:
   adding an extraction solvent to a sample to be tested to carry out extraction, and carrying out centrifugation and filtration to obtain a sample to be analyzed; and
   (2) testing:
   carrying out fluorescence detection on the sample to be analyzed to obtain fluorescence values at 433 nm and 650 nm, $I_{433}$ nm and $I_{650}$ nm, and then substituting the fluorescence values into an AFB1 standard curve to obtain a concentration of AFB1 in the sample to be tested.

14. The method according to claim 13, wherein the extraction solvent in step (1) is one of methanol/water, ethanol/water or acetonitrile/water with a volume fraction of 40%.

15. The method according to claim 13, wherein a ratio of the sample to be tested to the extraction solvent in step (1) is 1:3-5 in g/mL.

16. The method according to claim 13, wherein the AFB1 standard curve in step (2) is $I_{433}$ nm/$I_{650}$ nm=0.0627C−0.0068, $R^2$=0.9963, and a linear range is 0.03-10 ppb; and $I_{433}$ nm/$I_{650}$ nm=0.4825C−4.7038, $R^2$=0.9736, and a limit of detection is 0.012 ppb (S/N=3), wherein $I_{433}$ nm is the maximum fluorescence value of AFB1, $I_{650}$ nm is the maximum fluorescence value of β-CD@DNA-Cu NMs, and the ratio value of $I_{433}$ nm/$I_{650}$ nm represents the detection result; and C is the concentration of AFB1.

* * * * *